US007402431B2

(12) United States Patent
Har-Noy

(10) Patent No.: US 7,402,431 B2
(45) Date of Patent: *Jul. 22, 2008

(54) T-CELL THERAPY FORMULATION

(75) Inventor: Michael Har-Noy, Modi'in (IL)

(73) Assignee: Immunovative Therapies, Ltd., Shoham (IL)

( * ) Notice: Subject to any disclaimer, the term of this patent is extended or adjusted under 35 U.S.C. 154(b) by 160 days.

This patent is subject to a terminal disclaimer.

(21) Appl. No.: 11/069,010

(22) Filed: Mar. 1, 2005

(65) Prior Publication Data

US 2005/0214274 A1 Sep. 29, 2005

Related U.S. Application Data

(60) Provisional application No. 60/549,032, filed on Mar. 1, 2004.

(51) Int. Cl.
*C12N 5/06* (2006.01)
*C12N 16/00* (2006.01)
(52) U.S. Cl. .................................. 435/372.3; 530/391.1
(58) Field of Classification Search ........................ None
See application file for complete search history.

(56) References Cited

U.S. PATENT DOCUMENTS

| 5,806,529 | A | 9/1998 | Reisner et al. ............... 128/898 |
| 6,352,694 | B1 | 3/2002 | June et al. ................. 424/93.71 |
| 6,534,055 | B1 | 3/2003 | June et al. ................. 424/93.71 |
| 2002/0115214 | A1 | 8/2002 | June et al. ................. 435/372.3 |
| 2002/0127208 | A1 | 9/2002 | Waller et al. .............. 424/93.21 |
| 2004/0228848 | A1* | 11/2004 | Har-Noy .................. 424/93.71 |

FOREIGN PATENT DOCUMENTS

| WO | WO 03/038062 | 10/2002 |
| WO | WO 03024989 | * 3/2003 |

OTHER PUBLICATIONS

Antin, J. H. et al. (1992). "Cytokine Dysregulation and Acute Graft-Versus-Host Disease." *Blood*, vol. 80, No. 12: pp. 2964-2968.
Anderson, P. et al. (1988). "Crosslinking CD3 with CD2 Using Sepharose-Immobilized Antibodies Enhances T Lymphocyte Proliferation." *Cellular Immunology*, vol. 115, No. 2: pp. 246-256.
Asselin-Paturel et al. (1998). "Quantitative Analysis of Th1, Th2 and TGF-β1 Cytokine Expression in Tumor, TIL and PBL of Non-Small Cell Lung Cancer Patients." *Int. J. Cancer*, vol. 77, No. 1: pp. 7-12.
Bachmann, M. F. et al. (1997). "Distinct Roles for LFA-1 and CD28 During Activation of Naive T Cells: Adhesion Versus Costimulation." *Immunity*, vol. 7, No. 4: pp. 549-557.
Banu, N. et al. (1999). "TGF-β1 down-regulates induced expression of both class II MHC and B7-1 on primary murine renal tubular epithelial cells." *Kidney International*, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cells Activation with Immobilized Anti-CD3 and Mitogens." *Cellular Immunology*, vol. 120, No. 1: pp. 205-217.

Baxevanis, C. N. et al. (2000). "Compromised anti-tumor responses in tumor necrosis factor-α knockout mice." *Eur. J. Immunol.*, vol. 30, No. 7: pp. 1957-1966.
Belardelli, F. et al. (2002). "Cytokines as a link between innate and adaptive antitumor immunity." *Trends in Immunology*, vol. 23, No. 4: pp. 201-208.
Blazar, B. R. et al. (1997). "Recent advances in graft-versus-host disease (GVHD) prevention." *Immunological Reviews*, vol. 157: pp. 79-109.
Blazar, B. R. et al. (1998). "Rapamycin Inhibits the Generation of Graft-Versus-Host-Disease- and Graft-Versus-Leukemia-Causing T Cells by Interfering with the Production of Th1 or Th1 Cytotoxic Cytokines." *Journal of Immunology*, vol. 160, No. 11: pp. 5355-5365.
Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." *Transplantation*, vol. 63, No. 9: pp. 1307-1313.
Carpentier, A. F., G. Auf, et al. (2003). "CpG-oligonucleotides for cancer immunotherapy: review of the literature and potential applications in malignant glioma." *Front Biosci* 8: E115-27.
Chambers, C. A. et al. (1999). "Costimulatory regulation of T cell function." *Current Opinion in Cell Biology*, vol. 11, No. 2: pp. 203-210.
Champlin, R., I. Khouri, et al. (1999). "Allogenic hematopoietic transplantation as adoptive immunotherapy. Induction of graft-versus-malignancy as primary therapy." *Hematol Oncol Clin North Am* 13(5): 1041-57, vii-viii.
Champlin, R., K. van Besien, et al. (2000). "Allogeneic hematopoietic transplantation for chronic lymphocytic leukemia and lymphoma: potential for nonablative preparative regimens." *Curr Oncol Rep* 2(2): 182-91.
Chang, J. W., M. Peng, et al. (2000). "Induction of Th1 response by dendritic cells pulsed with autologous melanoma apoptotic bodies." *Anticancer Res* 20(3A): 1329-36.

(Continued)

*Primary Examiner*—Michail A Belyavskyi
(74) *Attorney, Agent, or Firm*—Z. Peter Sawicki; Westman, Champlin & Kelly, P.A.

(57) ABSTRACT

Ex-vivo prepared T-cells are harvested from cell culture conditions and formulated in medium suitable for infusion. The formulation is made by labeling the cells with one or more agents which have reactivity for T-cell surface moieties capable of delivery activation signals upon cross-linking and mixing the labeled cells with biodegradable nanospheres or microspheres coated with a material capable of cross-linking the agents attached to the T-cell surface moieties. Alternatively, the formulation may be made by mixing a population of T-cells with biodegradable nanospheres or microspheres coated with a first material and one or more second materials. The first material binds the second material and the second material has reactivity for surface moieties on the T-cells and the interaction of the second materials with the T-cells causes the activation of the T-cells. In either method, the mixture of T-cells and biodegradable spheres are suspended in a medium suitable for infusion, and the mixture is packaged in a container.

3 Claims, No Drawings

OTHER PUBLICATIONS

Chen, Q. et al. (1994). "Production of IL-10 by Melanoma Cells: Examination of its Role in Immunosuppression Mediated by Melanoma." *Int. J. Cancer*, vol. 56, No. 5: pp. 755-760.

Childs, R. et al. (2002). "Nonmyeloablative Stem Cell Transplantation for Solid Tumors: Expanding the Application of Allogenic Immunotherapy." *Seminars in Hematology*, vol. 39, No. 1: pp. 63-71.

Childs, R. et al. (2000). "Regression of metastatic renal-cell carcinoma after nonmyeloablative allogenic peripheral-blood stem-cell transplantation," *The New England Journal of Medicine*, vol. 343, No. 11: pp. 750-758.

Childs, R. W. (2000). "Nonmyeloablative allogeneic peripheral blood stem-cell transplantation as immunotherapy for malignant diseases." *Cancer J* 6(3): 179-87.

Childs, R. W. (2002). "Immunotherapy for solid tumors: nonmyeloablative allogeneic stem cell transplantation." *MedGenMed* 4(3): 13.

Clerici, M. et al. (1993). "A TH1—>TH2 switch is a critical step in the etiology of HIV infection." *Immunology Today*, vol. 14, No. 3: pp. 107-111.

Cohen, P. A., L. Peng, et al. (2000). "CD4+ T cells in adoptive immunotherapy and the indirect mechanism of tumor rejection." *Crit Rev Immunol* 20(1): 17-56.

Damle, N.K. et al. (1989). "Stimulation Via the CD3 and CD28 Molecules Induces Responsiveness to IL-4 in CD4+CD29+CD45R-Memory T Lymphocytes." *The Journal of Immunology*, vol. 143, No. 6: pp. 1761-1767.

Das, H., S. Imoto, et al. (2001). "Kinetic analysis of cytokine gene expression in patients with GVHD after donor lymphocyte infustion." *Bone Marrow Transplant* 27(4): 373-80.

Daubener, W. et al. (1995). "Establishment of T-helper type 1- and T-helper type 2-like human *Toxoplasma* antigen-specific T-cell clones." *Immunology*, vol. 86, No. 1: pp. 79-84.

Deeths, M. J. et al. (1999). "CD8+ T Cells Become Nonresponsive (Anergic) Following Activation in the Presence of Costimulation." *The Journal of Immunology*, vol. 163, No. 1: pp. 102-110.

De Vita, F., M. Orditura, et al. (2000). "Serum interleukin-10 is an independent prognostic factor in advanced solid tumors." *Oncol Rep* 7(2): 357-61.

de Waal Malefyt, R. et al. (1993). "Direct Effects of IL-10 on Subsets of Human CD4+ T Cell Clones and Resting T Cells. Specific Inhibition of IL-2 Production and Proliferation." *The Journal of Immunology*, vol. 150, No. 11: pp. 4754-4765.

D'Orazio, T. J. et al. (1998). "A Novel Role for TGF-β and IL-10 in the Induction of Immune Privilege." *The Journal of Immunology*, vol. 160, No. 5: 2089-2098.

Dudley, M. E. et al. (2002). "Cancer Regression and Autoimmunity in Patients After Clonal Repopulation with Antitumor Lymphocytes." *Science*, vol. 298, No. 5594: pp. 850-854.

Egeter, O. et al. (2000). "Eradication of Disseminated Lymphomas with CpG-DNA Activated T Helper 1 Cells from Nontransgenic Mice." *Cancer Research*, vol. 60, No. 6: 1515-1520.

Eibl, B. et al. (1996). "Evidence for a Graft-Versus-Tumor Effect in a Patient Treated With Marrow Ablative Chemotherapy and Allogeneic Bone Marrow Transplantation for Breast Cancer." *Blood*, vol. 88, No. 4: pp. 1501-1508.

Elsasser-Beile, U. et al. (1999). "Semiquantitative analysis of Th1 and Th2 cytokine expression in CD3+, CD4+, and CD8+ renal-cell-carcinoma-infiltrating lymphocytes." *Cancer Immunol Immunother*, vol. 48, No. 4: pp. 204-208.

Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." *Biotherapy* 9(4): 249-56.

Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." *J Drug Targt* 8(3): 173-84.

Fan, X. G., W. E., Liu, et al. (1998). "Circulating Th1 and Th2 cytokines in patients with hepatitis C virus infection." *Mediators Inflamm* 7(4): 295-7.

Finke, J. H., P. Rayman, et al. (1992). "Characterization of a human renal cell carcinoma specific cytotoxic CD8+ T cell line." *J Immunother* 11(1): 1-11.

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." *J Immunother Emphasis Tumor Immunol* 15(2): 91-104.

Flanagan, D. L. et al. (1999). "Th1 Cytokines and NK Cells Participate in the Development of Murine Syngeneic Graft-Versus-Host Disease." *The Journal of Immunology*, vol. 163, No. 3: pp. 1170-1177.

Fowler, D. H., J. Breglio, et al. (1996). "Allospecific CD4+, Th1/Th2 and CD8+, Tc1/Tc2 population in murine GVL: type I cells generate GVL and type II calls abrogate GVL." *Biol Blood Marrow Transplant* 2(3): 118-25.

Fowler, D. H. and R. E. Gress (2000). "Th2 and Tc2 cells in the regulation of GVHD, GVL, and graft rejection: considerations for the allogeneic transplantation therapy of leukemia and lymphoma." *Leuk Lymphoma* 38(3-4): 221-34.

Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." *Bone Marrow Transplant* 17(1): 13-8.

Freeman, G. J. et al. (2002). "Protect the killer: CTLs need defenses against the tumor." *Nature Medicine*, vol. 8, No. 8: pp. 787-789.

Friess, H., H. G. Berger, et al. (1996). "Treatment of advanced pancreatic cancer with mistletoe: results of a pilot trial." *Anticancer Res* 16(2): 915-20.

Fujimoto, T. et al. (1997). "Streptococcal Preparation OK-432 is a Potent Inducer of IL-12 and a T Helper Cell 1 Dominant State." *The Journal of Immunology*, vol. 158, No. 12: pp. 5619-5626.

Fujisao, S. et al. (1998). "Th1/Th2 balance alteration in the clinical course of a patient with pure red cell aplasia and thymoma." *British Journal of Haematology*, vol. 103, No. 2: pp. 308-310.

Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." *Cellular Immunology*, vol. 170, No. 1: pp. 111-119.

Gale, R. P. et al. (1984). "How Does Bone-Marrow Transplantation Cure Leukaemia?" *The Lancet*, vol. 2, No. 8393: pp. 28-30.

Garlie, N.K., A.V. LeFever, et al. (1999). "T cells coactivated with immobilized anti-CD3 and anti-CD28 as potential immunotherapy for cancer." *J Immunother* 22(4): 336-45.

Geppert, T.D. et al. (1988). "Activation of T Lymphocytes by Immobilized Monoclonal Antibodies to CD3, Regulatory Influences of Monoclonal Antibodies to Addition T Cell Surface Determinants." *J. Clin. Invest.*, vol. 81: pp. 1497-1505.

Ghosh, P., K. L. Komschlies, et al. (1995). "Gradual loss of T-helper 1 populations in spleen of mice during progressive tumor growth." *J Natl Cancer Inst* 87(19): 1478-83.

Gorelik, L., A. Prokhorova, et al. (1994). "Low-dose melphalan-induced shift in the production of a Th2-type cytokine to a Th1-type cytokine in mice bearing a large MOPC 315 tumor." *Cancer Immunol Immunother* 39(2): 117-26.

Grakoui, A. et al. (1999). "The Immunological Synapse: A Molecular Machine Controlling T Cell Activation." *Science*, vol. 285, No. 5425: pp. 221-227.

Granucci, F. et al. (2001). "Transcriptional reprogramming of dendritic cells by differentiation stimuli." *Eur J Immunol*, vol. 31, No. 9, pp. 2539-2546.

Grigg, A., P. Bardy, et al. (1999). "Fludarabine-based non-myeloablative chemotherapy followed by infusion of HLA-identical stem cells for relapsed leukaemia and lymphoma." *Bone Marrow Transplant* 23(2): 107-10.

Grohmann, U., M. C. Fioretti, et al. (1998). "Dendritic cells, interleukin 12, and CD4+ lymphocytes in the initiation of class I-restricted reactivity to a tumor/self peptide." *Crit. Rev. Immunol* 18(1-2): 87-98.

Hara, I., H. Hotta, et al. (1996). "Rejection of mouse renal cell carcinoma elicited by local secretion of interleukin-2." *Jpn J Cancer Res* 87(7): 724-9.

Heine, G. et al. (2002). "A shift in the Th(1)/Th(2) ratio accompanies the clinical remission of systemic lupus erythematosus in patients with end-stage renal disease." *Nephrology Dialysis Transplantation*, vol. 17, No. 10: pp. 1790-1794.

Heniford, B. T. et al. (1994). "Interleukin-8 Suppressed the Toxicity and Antitumor Effect of Interleukin-2." *Journal of Surgical Research*, vol. 56, No. 1: pp. 82-8.

Herlyn, D. and B. Birebent (1999). "Advances in cancer vaccine development." *Ann Med* 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." *Cancer Research*, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." *Anticancer Res* 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." *Cancer*, vol. 85, No. 11: pp. 2359-2367.

James, P. W. et al. (1999). "Aggregation of Lipid Rafts Accompanies Signaling Via the T Cell Antigen Receptor." *The Journal of Cell Biology*, vol. 147, No. 2: pp. 447-461.

Jung, U. et al. (Nov. 2003). "CD3/CD28-costimulated T1 and T2 subsets: differential in vivo allosensitization generates distinct GVT and GVHD effects." *Blood*, vol. 1, No. 9: pp. 3439-3446.

Kadowaki, N. et al. (2002). "Natural Type 1 Interferon-Producing Cells as a Link Between Innate and Adaptive Immunity." *Human Immunology*, vol. 63, No. 12: pp. 1126-1132.

Kai, S. and H. Hara (2003). "Allogeneic hematopoietic stem cells transplantation." *Therap Apher Dial* 7(3): 285-91.

Kasakura, S. (1998). "[A role for T-helper type 1 and type 2 cytokines in the pathogenesis of various human diseases]." *Rinsho Byori* 46(9): 915-21.

Kitahara, S., M. Ikeda, et al. (1996). "Inhibition of head and neck metastatic and/or recurrent cancer by local administration of multi-cytokine inducer OK-432." *J Laryngol Otol* 110(5): 449-53.

Knoefel, B., K. Nuske, et al. (1997). "Renal cell carcinomas produce IL-6, IL-10, IL-11, and TGF-beta 1 in primary cultures and modulate T lymphocyte blast transformation." *J Interferon Cytokine Res* 17(2): 95-102.

Kobayaski, M. et al. (1998). "A Pathogenic Role of Th2 Cells and Their Cytokine Products on the Pulmonary Metastasis of Murine B16 Melanoma." *The Journal of Immunology*, vol. 160, No. 12: pp. 5869-5873.

Kobayashi, M., R. B. Pollard, et al. (1997). "Inhibition of pulmonary metastasis by Z-100, an immunomodulatory lipid-arabinomannan extracted from Mycobacterium tuberculosis, in mice inoculated with B16 melanoma." *Anticancer Drugs* 8(2): 156-63.

Lahn, M. et al. (1999). "Pro-Inflammatory and T Cell Inhibitory Cytokines Are Secreted at High Levels in Tumor Cell Cultures of Human Renal Cell Carcinoma." *European Urology*, vol. 35, No. 1: pp. 70-80.

Langenkamp, A. et al. (2000). "Kinetics of dendritic cell activation: impact on priming, TH1, TH2 and nonpolarized T cells." *Nature Immunology*, vol. 1, No. 4: 311-316.

Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." *Clinical Immunology*, vol. 96, No. 3: pp. 187-197.

Le Bon, A. et al. (2002). "Links between innate and adaptive immunity via type I interferon." *Current Opinion Immunology*, vol. 14, No. 4. pp. 432-436.

Lee, P. P. et al. (1997). "T Helper 2-Dominant Antilymphoma Immune Response Is Associated With Fatal Outcome." *Blood*, vol. 90, No. 4: pp. 1611-1617.

Levine, B.L. et al. (1997). "Effects of CD28 Costimulation on Long-Term Proliferation of CD4+ T Cells in the Absence of Exogenous Feeder Cells." *The Journal of Immunology*, vol. 159, No. 12: pp. 5921-5930.

Li, L. et al. (1998). "Cyclophosphamide Given After Active Specific Immunization Augments Antitumor Immunity by Modulation of Th1 Commitment of CD4+ T Cells." *Journal of Surgical Oncology*, vol. 67, No. 4: pp. 221-227.

Liebowitz, D.N. et al. (1998). "Costimulatory approaches to adoptive immunotherapy." *Current Opinion Oncology*, vol. 10, No. 6: pp. 533-541.

Lowes, M. A., G. A. Bishop, et al. (1997). "T helper 1 cytokine mRNA is increased in spontaneously regressing primary melanomas." *J Invest Dermatol* 108(6): 914-9.

Ludviksson, B. R. et al. (2000). "The effect of TGF-β1 on immune responses of naive versus memory CD4+ Th1/Th2 T cells." *Eur J Immunol*, vol. 30, No. 7: pp. 2101-2111.

Lum, L.G. et al (2001). "Immune modulation in cancer patients after adoptive transfer of anti-CD3/anti-CD28-costimulated T-cells—phase I clinical trial." *Journal of Immunotherapy*, vol. 24, No. 5: pp. 408-419.

Ma, J. et al. (1998). "Use of encapsulated single chain antibodies for induction of anti-idiotypic humoral and cellular immune responses." *Journal of Pharmaceutical Sciences*, vol. 87, No. 11: pp. 1375-1378.

Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." *Cancer Immunol Immunother* 41(2): 111-21.

Maus, M. V. et al. (2002). "Ex vivo expansion of polyclonal and antigen-specific cytotoxic T lymphocytes by artificial APCs expressing ligands for the T-cell receptor, CD28 and 4-IBB." *Nature Biotechnology*, vol. 20, No. 2: pp. 143-148.

Menetrier-Caux, C. et al. (1999). "Renal cell carcinoma induces interleukin 10 and prostaglandin E2 production by monocytes." *British Journal of Cancer*, vol. 79, No. 1: pp. 119-130.

Moran, M. et al. (1998). "Engagement of GPI-Linked CD48 Contributes to TCR Signals and Cytoskeletal Reorganization: A Role for Lipid Rafts in T Cell Activation." *Immunity*, vol. 9, No. 6: pp. 787-796.

Muller, M. et al. (2003). "Surface modification of PLGA microspheres." *Journal of Biomedic Material Research*, vol. 66A, No. 1: pp. 55-61.

Nabioullin, R. et al. (1994). "Interleukin-10 is a potent inhibitor of tumor cytotoxicity by human monocytes and alveolar macrophages." *Journal of Leukocyte Biology*, vol. 55, No. 4: pp. 437-442.

Nakagomi, H. et al. (1995). "Lack of Interleukin-2 (IL-2) Expression and Selective Expression of IL-10 mRNA in Human Renal Cell Carcinoma." *Int. Journal of Cancer*, vol. 63, No. 3: pp. 366-371.

Nishimura, T. et al. (2000). "The critical role of Th1-dominant immunity in tumor immunology." *Cancer Chemother Pharmacol*, vol. 46 (Suppl): S52-S61.

Nitta, T., M. Hishii, et al. (1994). "Selective expression of interleukin-10 gene within glioblastoma multiforme." *Brain Res* 649(1-2): 122-8.

O'Donnell P.B. et al. (1997). "Preparation of microspheres by the solvent evaporation technique." *Advanced Drug Delivery Reviews*, vol. 28, No. 1: pp. 25-42.

Oka, H. et al. (1999). "An immunomodulatory arabinomannan extracted from Mycobacterium tuberculosis, Z-100, restores the balance of Th1/Th2 cell responses in tumor bearing mice." *Immunology Letters*, vol. 70, No. 2: pp. 109-117.

Okamoto, T. et al. (1997). "Local Injection of OK432 Can Augment the TH1-Type T-Cell Response in Tumor-Draining Lymph Node Cells and Increase Their Immunotherapeutical Potential." *International Journal of Cancer*, vol. 70, No. 5: pp. 598-605.

Okutomi, T., Y. Kato, et al. (2000). "[Clinical effects of adjuvant therapy using Z-100 (Ancer 20 injection) for oral cancer—prevention of stomatitis and hematopoietic impairment]." *Gan To Kagaku Ryoho* 27(1): 65-71.

Onishi, T. et al. (1999). "An assessment of the immunological environment based on intratumoral cytokine production in renal cell carcinoma." *BJU International*, vol. 83, No. 4: pp. 488-492.

Raghupathy, R. (1997). "Th1-type immunity is incompatible with successful pregnancy." *Immunology Today*, vol. 18, No. 10: pp. 478-482.

Raghupathy, R. et al. (1999). "Maternal Th1- and Th2-Type Reactivity to Placental Antigens in Normal Human Pregnancy and Unexplained Recurrent Spontaneous Abortions." *Cellular Immunology*, vol. 196, No. 2: pp. 122-130.

Rondon, G., S. Giralt, et al. (1996). "Graft-versus leukemia effect after allogeneic bone marrow transplantation for chronic lymphocytic leukemia." *Bone Marrow Transplant* 18(3): 669-72.

Rosenberg, S. A. (2001). "Progress in the development of immunotherapy for the treatment of patients with cancer." *Journal of Internal Medicine*, vol. 250, No. 6: pp. 462-475.

Roussel, E. et al. (1996). "Predominance of a type 2 intratumoral immune response in fresh tumor-infiltrating lymphocytes from human gliomas." *Clinical and Experimental Immunology*, vol. 105, No. 2: pp. 344-352.

Rubbi, C.P. et al. (1993). "Evidence of surface antigen detachment during incubation of cells with immunomagnetic beads." *Journal of Immunology Methods*, vol. 166, No. 2: pp. 233-241.

Santin, A. D. et al. (2000). "Interleukin-10 Increases Th1 Cytokine Production and Cytotoxic Potential In Human Papillomavirus-Specific CD8(+) Cytotoxic T Lymphocytes." *Journal of Virology*, vol. 74, No. 10: pp. 4729-4737.

Sato, M., S. Goto, et al. (1998). "Impaired production of Th1 cytokines and increased frequency of Th2 subsets in PBMC from advanced cancer patients." *Anticancer Res* 18(5D): 3951-5.

Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity." *Blood*, vol. 89, No. 7: pp. 2529-2536.

Shibuya, T.Y. et al. (2000). "Anti-CD3/Anti-CD28 Bead Stimulation Overcomes CD3 Unresponsiveness in Patients With Head and Neck Squamous Cell Carcinoma." *Arch Otolaryngol Head Neck Surg*, vol. 126, No. 4: 473-479.

Shinomiya, Y., M. Harada, et al. (1995). "Anti-metastatic activity induced by in vivo activation of purified protein derivative (PPD)-recognizing Th1 type CD4+ T Cells." *Immunobiology* 193(5): 439-55.

Shurin, M. R., L. Lu, et al. (1999), "Th1/Th2 balance in cancer, transplantation and pregnancy." *Springer Semin Immunopathol* 21(3): 339-59.

Slavin, S. et al. (2001). "Non-myeloablative allogeneic Stem cell transplantation focusing on immunotherapy of life-threatening malignant and non-malignant diseases." *Critical Reviews Oncology Hematology*, vol. 39, No. 1-2: pp. 25-29.

Slavin, S. et al. (1995). "Allogenic cell therapy for relapsed leukemia after bone marrow transplantation with donor peripheral blood lymphocytes." *Experimental Hematology*, vol. 23, No. 14: pp. 1553-1562.

Slavin, S. et al. (1996). "Allogenic Cell Therapy With Donor Peripheral Blood Cells and Recombinant Human Interleukin-2 to Treat Leukemia Relapse After Allogenic Bone Marrow Transplantation." *Blood*, vol. 87, No. 6: pp. 2195-1204.

Slavin, S. et al. (1996). "Allogenic Cell Therapy: The Treatment of Choice for All Hematologic Malignancies Relapsing Post BMT." *Blood*, vol. 87, No. 9: pp. 4011-4013.

Slavin, S. et al. (2001). "Nonmyeloablative stem cell transplantation for the treatment of cancer and life-threatening nonmalignant disorders: past accomplishments and future goals." *Cancer Chemother. Pharmacol*, vol. 48, (Suppl 1): pp. S79-S84.

Slavin, S. et al. (1998). "Immunotherapy in conjunction with autologous and allogeneic blood or marrow transplantation in lymphoma." *Annals of Oncology*, vol. 9 (Suppl 1): pp. S31-S39.

Smith, D. R., S. L. Kunkel, et al. (1994). "Production of interleukin-10 by human bronchogenic carcinoma." *Am J Pathol* 145(1): 18-25.

Smyth, M. J. et al. (2002). "New Aspects of Natural-Killer-Cell Surveillance and Therapy of Cancer." *Nature Reviews Cancer*, vol. 2, No. 11: pp. 850-861.

Sredni, B. et al. (1995). "Bone Marrow-Sparing and Prevention of Alopecia by AS101 in Non-Small-Cell Lung Cancer Patients Treated with Carboplatin and Etoposide." *Journal of Clinical Oncology*, vol. 13, No. 9: pp. 2342-2353.

Sredni, B. et al. (1996). "Predominance of TH1 Response in Tumor-Bearing Mice and Cancer Patients Treated with AS101." *National Journal of Cancer Institute*, vol. 88, No. 18: pp. 1276-1284.

Sredni, B., R. H. Xu, et al. (1996). "The protective role of the immunomodulator AS101 against chemotherapy-induced alopecia studies on human and animal models." *Int J Cancer* 65(1): 97-103.

Stein, G., W. Henn, et al. (1998). "Modulation of the cellular and humoral immune responses of tumor patients by mistletoe therapy." *Eur J Med Res* 3(4): 194-202.

Stern, B. V. et al. (2002). "Vaccination with Tumor Peptide in CpG Adjuvant Protects Via IFN-Gamma-Dependent CD4 Cell Immunity." *The Journal of Immunology*, vol. 168, No. 12: pp. 6099-6105.

Tabata, T. et al. (1999). "Th2 Subset Dominance Among Peripheral Blood T Lymphocytes in Patients with Digestive Cancers." *American Journal of Surgery*, vol. 177, No. 3: pp. 203-208.

Taga, K. et al. (1993). "Human Interleukin-10 Can Directly Inhibit T-Cell Growth." *Blood*, vol. 81, No. 11: pp. 2964-2971.

Takeuchi, T. et al. (1997). "Th2-like response and antitumor effect of anti-interleukin-4 mAb in mice bearing renal cell carcinoma." *Cancer Immunol Immunother*, vol. 43, No. 6: pp. 375-381.

Tanaka, K., K. Kemmotsu, et al. (1998). "[Flow cytometric analysis of helper T cell subets (Th1 and Th2) in healthy adults]." *Rinsho Byori* 46(12): 1247-51.

Tanaka, J., M. Imamura, et al. (1997). "The important balance between cytokines derived from type 1 and type 2 helper T cells in the control of graft-versus-host disease." *Bone Marrow Transplant* 19(6): 571-6.

Tatsumi, T. et al. (2002). "Disease-associated bias in T helper type 1 (Th1)/Th2 CD4(+) T cell responses against MAGE-6 in HLA-DRB10401(+) patients with renal cell carcinoma or melanoma." *Journal of Experimental Medicine*, vol. 196, No. 5: pp. 619-628.

Terao, H., M. Harada, et al. (1994). "Th1 type CD4+ T cells may be a potent effector aginst poorly immunogenic syngeneic tumors." *Biotherapy* 8(2): 143-51.

Tessmar, J. et al. (2003). "The use of poly(ethylene glycol)-block-poly(lactic acid) derived copolymers for the rapid creation of biomimetic surfaces." *Biomaterials*, vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." *Cancer Immunol Immunother* 40(2): 103-8.

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." *Clinical Immunology*, vol. 105, No. 3: pp. 259-272.

Thomas, E., R. Storb, et al. (1975). "Bone-marrow transplantation (first of two parts)." *N Engl J Med* 292(16): 832-43.

Thomas, E. D., R. Storb, et al. (1975). "Bone-marrow transplantation (second of two parts)." *N Engl J Med* 292(17): 895-902.

Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." *Blood*, vol. 83, No. 1: pp. 113-118.

To, W. C. et al. (2000). "Therapeutic Efficacy of Th1 and Th2 L-selectin—CD4+ Tumor-Reactive T Cells." *Laryngoscope* vol. 110, (10 Pt 1): pp. 1648-1654.

Ueno, N. T., G. Rondon, et al. (1998). "Allogeneic peripheral-blood progenitor-cell transplantation for poor-risk patients with metastatic breast cancer." *J Clin Oncol* 16(3): 986-93.

van Besien, K., P. Thall, et al. (1997). "Allogenic transplantation for recurrent or refractory non-Hodgkin's lymphoma with poor prognostic features after conditioning with thiotepa, busulfan, and cyclophosphamide: experience in 44 consecutive patients." *Biol Blood Marrow Transplant* 3(3): 150-6.

Voutsadakis, I.A. (2003). "NK cells in allogeneic bone marrow transplantation." *Cancer Immunol Immunother*, vol. 52, No. 9: pp. 525-534.

Vowels, B. R. et al. (1994). "Th2 Cytokine mRNA Expression in Skin in Cutaneous T-Cell Lymphoma." *The Journal of Investigative Dermatology*, vol. 103, No. 5: pp. 669-673.

Wang, Q. et al. (1995). "Selective Cytokine Gene Expression in Renal Cell Carcinoma Tumor Cells and Tumor-Infiltrating Lymphocytes." *International Journal of Cancer*, vol. 61, No. 6: pp. 780-785.

Weber, K., U. Mengs, et al. (1998). "Effects of a standardized mistletoe preparation on metastatic B16 melanoma colonization in murine lungs." *Arzneimittelforschung* 48(5): 497-502.

Weiden, P. L. et al. (1981). "Antileukemic Effect of Chronic Graft-Versus-Host Disease: Contribution to Improved Survival After Allogenic Marrow Transplantation." *New England Journal of Medicine*, vol. 304 No. 25: pp. 1529-1533.

Whitemore, M. et al. (1999). "LPD lipopolyplex initiates a potent cytokine response and inhibits tumor growth." *Gene Therapy*, vol. 6, No. 11: pp. 1867-1875.

Wong, B. R. et al. (1999). "Trance is a TNF family member that regulates dendritic cell and osteoclast function." *Journal of Leukocyte Biology*, vol. 65, No. 6: pp. 715-724.

Woo, E. Y. et al. (2001). "Regulatory CD4(+)CD25(+) T Cells in Tumors from Patients with Early-Stage Non-Small Cell Lung Cancer and Late-Stage Ovarian Cancer." *Cancer Research*, vol. 61, No. 12: pp. 4766-4772.

Woo, E. Y. et al. (2002). "Cutting edge: Regulatory T Cells from Lung Cancer Patients Directly Inhibit Autologous T cell proliferation." *J Immunol* 168(9): 4272-6.

Yamamura, M. (1992). "Defining protective responses to pathogens: cytokine profiles in leprosy lesions." *Science* 255(5040): 12.

Yashiro-Ohtani, Y. et al. (2000). "Non-CD28 Costimulatory Molecules Present in T Cell Rafts Induce T Cell Costimulation by Enhancing the Association of TCR with Rafts." *The Journal of Immunology*, vol. 164, No. 3: pp. 1251-1259.

Yoon, T. J. et al. (1998). "Prophylactic effect of Korean mistletoe (*Viscum album coloratum*) extract on tumor metastasis is mediated by enhancement of NK cell activity." *International Journal of Immunopharmacology*, vol. 20, No. 4-5: pp. 163-172.

Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." *Journal of Experimentive Medicine*, vol. 183, No. 1: pp. 87-97.

\* cited by examiner

T-CELL THERAPY FORMULATION

The present application claims priority of U.S. provisional patent application Ser. No. 60/549,032, filed Mar. 1, 2004, entitled Cell Therapy Formulation Method and Composition.

FIELD OF INVENTION

This invention relates to methods for formulating ex-vivo prepared T-cells for infusion.

BACKGROUND OF THE INVENTION

Cell therapy methods have been developed in order to enhance the host immune response to tumors, viruses and bacterial pathogens. Cell therapy methods often involve the ex-vivo activation and expansion of T-cells. Examples of these type of treatments include the use of tumor infiltrating lymphocyte (TIL) cells (see U.S. Pat. No. 5,126,132 issued to Rosenberg), cytotoxic T-cells (see U.S. Pat. No. 6,255,073 issued to Cai, et al.; and U.S. Pat. No. 5,846,827 issued to Celis, et al.), expanded tumor draining lymph node cells (see U.S. Pat. No. 6,251,385 issued to Terman), and various other lymphocyte preparations (see U.S. Pat. No. 6,194,207 issued to Bell, et al.; U.S. Pat. No. 5,443,983 issued to Ochoa, et al.; U.S. Pat. No. 6,040,177 issued to Riddell, et al.; U.S. Pat. No. 5,766,920 issued to Babbitt, et al.).

For maximum effectiveness of T-cells in cell therapy protocols, the ex vivo activated T-cell population should be in a state of maximal activation upon infusion. Efforts for developing improved methods for producing more effective T-cells for use in cell therapy protocols have focused on the ex-vivo activation methods. However, ex-vivo activated cells need to be harvested and administered to patients to have a therapeutic effect. The harvesting of the T-cells removes them from the activating stimuli available in the ex-vivo cultures. Therefore, the longer the time from harvest to infusion, the lower the quality of the T-cells.

There is a need to develop T-cell formulations for infusion that maintain the cells in a state that can maximally orchestrate an immune response to cancer, infectious diseases and other disease states at both the time of infusion and while circulating in the blood. Efforts to maintain the activation state of T-cells at the time of infusion have most commonly involved the formulation of the T-cells with exogenous IL-2. Systemic IL-2 administration to patients has also been used to maintain the activation state of T-cells post-infusion. However, exogenous IL-2 administration is extremely toxic to patients and has not resulted in significant benefit to patients undergoing T-cell infusions.

SUMMARY OF THE INVENTION

This invention includes ex-vivo prepared T-cells which are harvested from cell culture conditions and formulated in media suitable for infusion. The method of formulation involves: (1) labeling the cells with one or more agents which have reactivity for T-cell surface moieties capable of delivering activation signals upon cross-linking; (2) mixing the labeled cells with biodegradable nanospheres or microspheres coated with a material capable of cross-linking the agents attached to the T-cell surface moieties; (3) suspending the mixture of labeled T-cells and coated biodegradable cross-linking spheres in a medium suitable for infusion; (4) packaging the mixture in a suitable container, such as a syringe or an IV infusion bag; and (5) parenteral administration of said mixture to a patient.

Alternatively, the invention can be accomplished with a formulation method which involves: (1) mixing a population of T-cells with biodegradable nanospheres or microspheres coated with a first material and one or more second materials, whereas the first material binds the second materials and the second materials have reactivity for surface moieties on the T-cells, and whereas the interaction of the second materials with the T-cells causes the activation of the T-cells; (2) suspending the mixture of T-cells and the biodegradable spheres in a medium suitable for infusion; and (3) packaging the mixture in a suitable container, such as a syringe or an IV infusion bag; and (4) parenteral administration of the mixture to a patient.

In practice of the present invention, the T-cells intended for infusion are first harvested from the ex-vivo cell culture environment. The harvested cells are then either immediately formulated for infusion, cryopreserved for later formulation, or shipped to the patient location for formulation.

Upon formulation by the method of the present invention, all the T-cells for infusion will be maximally activated in a non-toxic delivery vehicle.

For the purposes of the present invention, all references to T-cells includes a population of cells with at least a portion of the cells containing T-cells. T-cells are cells which express TCR, including $\alpha/\beta$ and $\gamma/\delta$ TCRs. T-cells include all cells which express CD3, including T-cell subsets which also express CD4 and CD8. T-cells include both naïve and memory cells and effector cells such as CTL. T-cells also include regulatory cells such as Th1, Tc1, Th2, Tc2, Th3, Treg, and Trl cells. T-cells also include NKT-cells and similar unique classes of the T-cell lineage.

PREFERRED EMBODIMENTS

The biodegradable spheres of the present invention are preferably manufactured from aliphatic polyesters, such as poly(lactic acid) (PLA), poly(glycolic acid) (PGA), copolymers of PLA and PGA (PLGA) or poly(carprolactone) (PCL), and polyanhydrides. The spheres are produced into small particle sizes of 0.1 to 500 microns, preferably less than 10 microns and most preferably less than 1 micron. Microspheres of this size range are capable of direct injection into the body by conventional methods. It is preferred that the coated spheres be designed to degrade in physiological fluids within 7 days, more preferably within 3 days.

The preferred first material for coating on the biodegradable spheres is polyclonal goat (or sheep) anti-mouse polyclonal antibodies. By way of example, this preferred first material can be used to cross-link mouse-derived monoclonal antibodies, or fragments or genetically engineered derivatives thereof, that have specificity for T-cell surface moieties. Thus, for example, the mixing of goat anti-mouse coated microspheres (or nanospheres) with human T-cells-labeled with mouse anti-human CD3 and mouse anti-human CD28 mAbs will cause the cross-linking of the mouse mAbs on the human T-cells through the binding of the goat anti-mouse polyclonal antibody with the mouse mAbs. The cross-linking of the mAbs causes the activation of the T-cells. Alternatively, the anti-human CD3 and anti-CD28 can also be first bound, preferably in a 50/50 ratio, on the goat (or sheep) polyclonal antibody coated spheres and mixed with the T-cells. It will be obvious to those skilled in the art that many combinations of first materials and second materials can be used to accomplish the objective of cross-linking second agents attached to T-cell surface moieties in order to initiate signal transduction and activation of T-cells.

The mixture of T-cells with cross-linked surface moieties is suspended in infusion medium (e.g., isotonic solutions such as normal saline, 5% dextrose, Plasma-Lyte (Baxter) or Normasol (Abbott). In some embodiments, the infusion medium is supplemented with 0.5%-10% human serum albumen (HSA).

The mixture is preferably adjusted to a final T-cell concentration of between $1\times10^7$ to $1\times10^8$ cells per ml of infusion media. In a preferred embodiment, $10^9$ T-cells are formulated in 100 ml of infusion media. The formulation is then packaged in one or more containers, such as syringes, plastic pouches, or plastic bottles.

Although the present invention has been described with reference to preferred embodiments, workers skilled in the art will recognize that changes may be made in form and detail without departing from the spirit and scope of the invention.

What is claimed is:

1. A composition comprising a treatment effective amount of cells, of which a portion are T-cells, whereby said T-cells are contacted with one or more first agents that ligate a cell surface moiety on at least a portion of the T-cells, and whereby the first agents are cross-linked by a second agent attached to a biodegradable support to activate the T-cells, and whereby said activated T-cells and biodegradable supports are suspended in a medium suitable for parenteral infusion in an activated state at a concentration of at least $10^7$ cells per ml of the medium and packaged in a suitable container for administration of said composition to a patient.

2. The composition of claim 1 whereby the container is collapsible comprising opposing walls of flexible material and a flexible tube protruding from the container.

3. The composition of claim 1 whereby the container is a syringe.

* * * * *